United States Patent
Gavhane et al.

(10) Patent No.: US 12,152,000 B2
(45) Date of Patent: Nov. 26, 2024

(54) PROCESS FOR MAKING A PHARMACEUTICAL COMPOUND

(71) Applicant: Adeptio Pharmaceuticals Limited, London (GB)

(72) Inventors: Kishor Bapu Gavhane, Mumbai (IN); Nitin Punjaji Lad, Mumbai (IN); Ramakrishna Guduru, Mumbai (IN); Sunit Ramesh Kulkarni, Mumbai (IN)

(73) Assignee: ADEPTIO PHARMACEUTICALS LIMITED, London (GB)

( * ) Notice: Subject to any disclaimer, the term of this patent is extended or adjusted under 35 U.S.C. 154(b) by 0 days.

(21) Appl. No.: 18/299,191

(22) Filed: Apr. 12, 2023

(65) Prior Publication Data
US 2023/0331667 A1    Oct. 19, 2023

(30) Foreign Application Priority Data

Apr. 13, 2022  (IN) .............................. 202211022077
May 30, 2022  (EP) ..................................... 22176081

(51) Int. Cl.
*C07C 313/20* (2006.01)
*B01J 27/128* (2006.01)

(52) U.S. Cl.
CPC ........... *C07C 313/20* (2013.01); *B01J 27/128* (2013.01)

(58) Field of Classification Search
None
See application file for complete search history.

(56) References Cited

U.S. PATENT DOCUMENTS

| 2,830,993 A | 4/1958 | Brossi et al. |
| 2,843,591 A | 7/1958 | Brossi et al. |
| 3,045,021 A | 7/1962 | Brossi et al. |

FOREIGN PATENT DOCUMENTS

| KR | 101102957 B1 | 1/2012 |
| KR | 101409335 B1 | 6/2014 |

OTHER PUBLICATIONS

Reddy et al. (Tetrahedron Letters, 2014, 55, 3157). (Year: 2014).*
Yao et al., European Journal of. Medicinal. Chemistry 46., (2011), 1841-1848.
Paek et al., Chemistry a European Journal, 2010, 16, (2010) 4623-4628.
Reddy et al., Tetrahedron Lett., 2012, 53(51), 6916-6918.
Extended European Search Report dated Oct. 28, 2022 in connection with EP22176081.2.
Nakamura et al., Journal of American Chemical Society vol. 118, No. 35, 1996, 8489-8490.

* cited by examiner

*Primary Examiner* — Sudhakar Katakam
*Assistant Examiner* — Jennifer C Sawyer
(74) *Attorney, Agent, or Firm* — Heslin Rothenberg Farley & Mesiti P.C.

(57) ABSTRACT

This invention relates to a novel process for making dihydrotetrabenazines, and in particular (+)-α-dihydrotetrabenazine, novel synthetic intermediates for use in the process and processes for making the intermediates.

18 Claims, No Drawings

PROCESS FOR MAKING A PHARMACEUTICAL COMPOUND

CROSS REFERENCE TO RELATED APPLICATIONS

This application claims priority to IN 202211022077, filed Apr. 13, 2022, and to EP 22176081.2, filed May 30, 2022. The entire contents of both priority documents are hereby incorporated by reference herein.

This invention relates to a novel process for making dihydrotetrabenazines, and in particular (+)-α-dihydrotetrabenazine, novel synthetic intermediates for use in the process and processes for making the intermediates.

BACKGROUND OF THE INVENTION (+)-α-Dihydrotetrabenazine is an inhibitor of the type 2 vesicular monoamine transporter (VMAT2) and has been disclosed as being useful in the treatment of hyperkinetic movement disorders and hypokinetic movement disorders, see for example WO 2018/178233.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

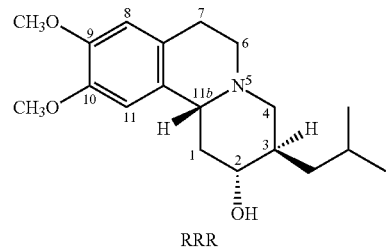
RRR

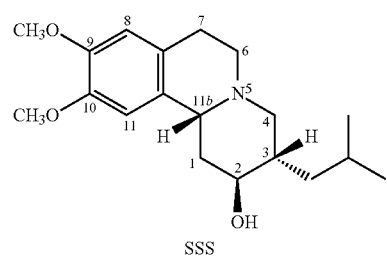
SSS

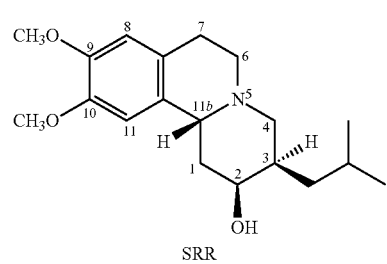
SRR

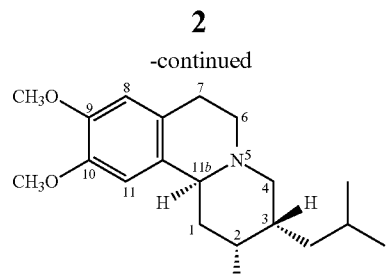
RSS

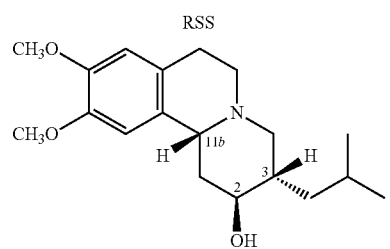
SSR

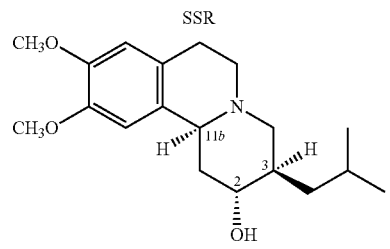
RRS

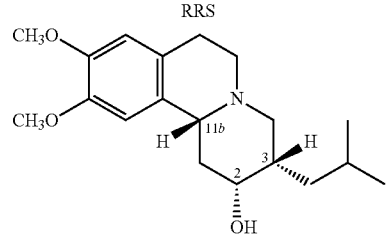
RSR

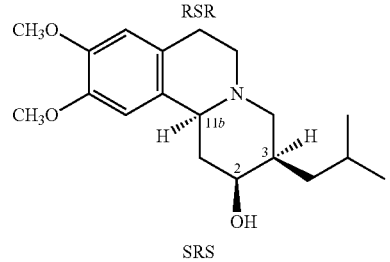
SRS

The stereochemistry of each isomer is defined using the "R and S" nomenclature developed by Cahn, Ingold and Prelog, see *Advanced Organic Chemistry* by Jerry March, 4$^{th}$ Edition, John Wiley & Sons, New York, 1992, pages 109-114. In this patent application, the designations "R" or "S" are given in the order of the position numbers of the carbon atoms 2, 3 and 11b. Thus, the 2R,3S,11bS isomer is referred to in shorthand form as RSS and so on.

(+)-α-Dihydrotetrabenazine has the RRR configuration shown above.

Dihydrotetrabenazines have typically been prepared by the reaction of tetrabenazine with a reducing agent suitable for reducing the ketone group to an alcohol. Illustrative of this process are the procedures disclosed in U.S. Pat. No. 2,843,591 (Brossi et al., 1958).

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders such as Huntington's disease, hemiballismus, senile chorea, tic, tardive dyskinesia and Tourette's syndrome, see for example Jankovic et al., *Am. J. Psychiatry.* (1999) August; 156(8):1279-81 and Jankovic et al., *Neurology* (1997) February; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks postsynaptic dopamine receptors.

The chemical structure of tetrabenazine is as shown below.

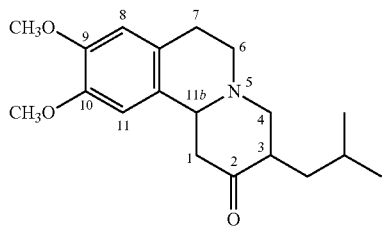

Structure of tetrabenazine

The compound has chiral centres at the 3 and 11b carbon atoms and hence can, theoretically, exist in a total of four isomeric forms, as shown below.

Commercially available tetrabenazine is a racemic mixture of the RR and SS isomers and it would appear that the RR and SS isomers are the most thermodynamically stable isomers.

Because of the numbers of chiral centres present in tetrabenazine and dihydrotetrabenazines, known processes for the synthesis of individual isomers of dihydrotetrabenazines have required a step of resolving mixtures of isomers.

For example, the synthesis and characterisation of all eight dihydrotetrabenazine isomers is described by Sun et al. (*Eur. J. Med. Chem.* (2011), 1841-1848). IN order to reduce the number of individual isomers requiring separation, Sun et al synthesized (+)-α-dihydrotetrabenazine by first resolving (RR/SS) tetrabenazine to give purified (+) tetrabenazine (RR) which they then reduced using several different sets of reducing conditions. Reduction using sodium borohydride gave a mixture of (+)-α-dihydrotetrabenazine and (+)-β-dihydrotetrabenazine (RRR & SRR isomers) which proved extremely difficult to purify using column chromatography or recrystallization. The use of borane at low temperature (−20° C.) gave better stereoselectivity and resulted in a 19:1 mixture of the (+)-α-isomer and (+)-β-isomer, from which the (+)-α-dihydrotetrabenazine could be isolated in pure form by recrystallisation from acetone-water.

The first synthesis of tetrabenazine was disclosed in U.S. Pat. No. 2,830,993 (Brossi et al. 1958) and involved the Dieckmann cyclisation, hydrolysis and decarboxylation of 1-carbethoxymethyl-2-(2,2-dicarbomethoxy-4-methyl-n-pentyl)-6,7-dimethoxy-1,2,3,4-tetrahydroisoquinoline, which has the chemical structure:

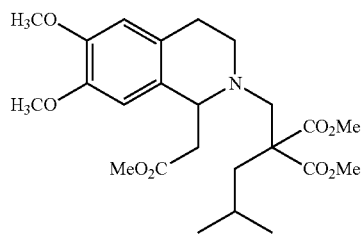 [SMILES: COC(=O)CC1c2cc(OC)c(OC)cc2CCN1CC(CC(C)C)(C(=O)OC)C(=O)OC]

In an alternative synthesis, disclosed in U.S. Pat. No. 3,045,021 (Brossi et al. 1962), tetrabenazine is formed by the reaction of 6,7-dimethoxy-3,4-dihydroisoquinoline with 3-methylene-5-methyl-2-hexanone.

A commercial process for making tetrabenazine involves a variation of the Brossi (1962) synthesis in which tetrabenazine is formed by the reaction of 6,7-dimethoxy-3,4-dihydroisoquinoline with 3-(N,N-dimethylaminomethyl-5-methyl-2-hexanone.

A significant disadvantage of known processes of making (+)-α-dihydrotetrabenazine which proceed via tetrabenazine is that a separation of optical isomers is required either before the reduction of the tetrabenazine (as described in Sun et al. (2011) or after the reduction of tetrabenazine (which gives a mixture of dihydrotetrabenazine isomers). A consequence of having to carry out the chiral separation step at a late stage in the synthetic route, either on a mixture of tetrabenazine optical isomers, or on a mixture of dihydrotetrabenazine isomers, or both, is that in order to produce (+)-α-dihydrotetrabenazine, at least 50% of the tetrabenazine or dihydrotetrabenazine must be discarded because it is in the wrong isomeric form.

Paek et al, Chem. Eur. J. 2010, 16, 4623-4628, discloses a total synthesis of (+)-α-dihydrotetrabenazine in which a desired stereochemistry is introduced at an early state in the synthesis and is then maintained through a series of stereospecific reactions to give (+)-α-dihydrotetrabenazine whilst avoiding the need for wasteful separations of isomers. The Paek et al. synthesis is shown in Scheme 1 below. This process is also disclosed in KR101102957 E1.

Scheme 1

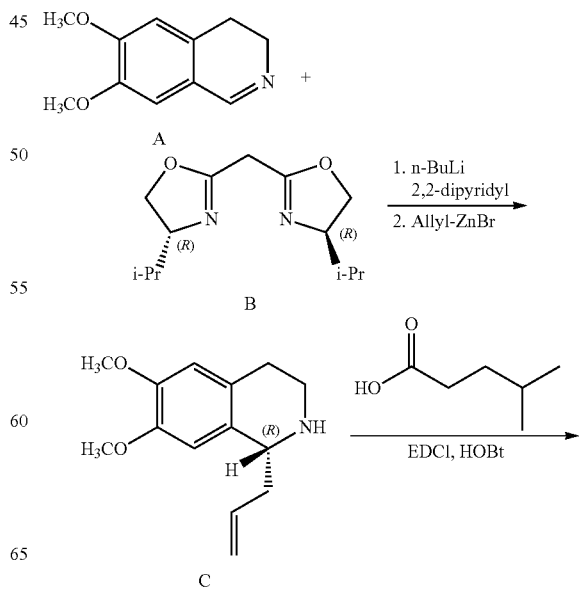

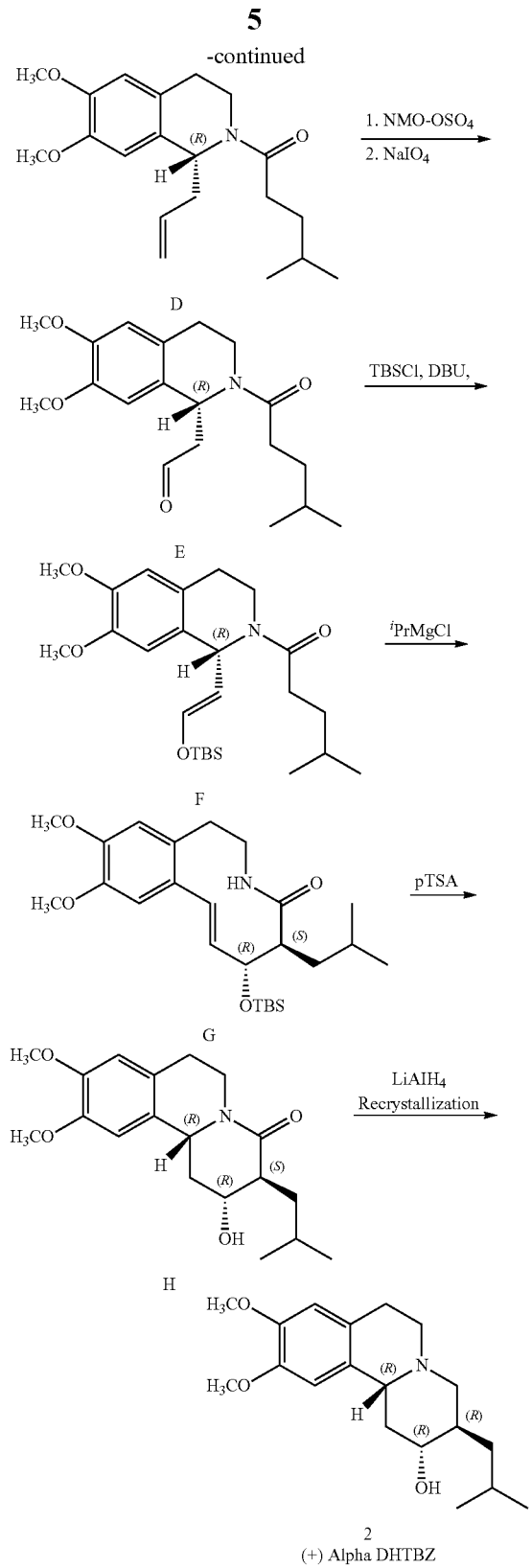

In the Paek et al. synthesis, the commercially available 6,7-dimethoxy-3,4-dihydroisoquinoline A is subjected to an asymmetric allylation reaction using the chiral auxiliary B and the process described in M. Nakamura et al. J. Am. Chem. Soc. 1996, 118, 8489-8490. to give the enantiomerically enriched 1-allyl-6,7-dimethoxy-tetrahydroisoquinoline C which is then reacted with 4-methylvaleric acid under amide bond-forming conditions in the presence of EDCI and HOBt to give the amide D. The olefinic bond of the allylic group in amide D is oxidatively cleaved using osmium tetroxide followed by sodium periodate to form the aldehyde E which is converted into enol silyl ether F by reaction with tert-butyldimethylsilyl chloride in the presence of DBU. Reaction of the enol silyl ether F with the Grignard reagent isopropylmagnesium bromide leads to a [3,3]-sigmatropic Aza-Claisen rearrangement taking place to give the ten-membered lactam G in which the stereochemistry of the isobutyl and OTBS groups corresponds to the stereochemistry required for (+)-α-dihydrotetrabenazine. Treatment with toluene-sulfonic acid gives rise to a diastereoselective ring closure to the benzoisoquinolizidine lactam H which is then reduced to give (+)-α-dihydrotetrabenazine.

In the process described in Paek et al. the stereochemistry of the final product ((+)-α-dihydrotetrabenazine) is determined by the use of particular chiral reagents at a very early stage in the synthesis. Therefore, the process avoids the need for wasteful chiral separations in the final step or penultimate step, a problem with previous processes for the preparation of ((+)-α-dihydrotetrabenazine which have involved either the resolution of racemic mixtures of (±)-α-dihydrotetrabenazine or the resolution of racemic (±)-tetrabenazine followed by a stereospecific reduction.

However, two significant drawbacks of the Paek et al. process are that the formation of the 1-allyl-6,7-dimethoxy-tetrahydroisoquinoline C involves the use of lithium chemistry at low temperatures (−70°) and the relatively expensive chiral auxiliary compound:

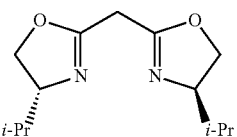 [SMILES: CC(C)[C@@H]1COC(CC2=N[C@H](C(C)C)CO2)=N1]

These two drawbacks mean that the process of making the key chiral intermediate, 1-allyl-6,7-dimethoxy-tetrahydroisoquinoline C, described in Paek et al. and Nakamura et al. is not ideally suited to scale up for use on a commercial scale.

Accordingly, there is a need for a process for making the chiral intermediate 1-allyl-6,7-dimethoxy-tetrahydroisoquinoline C which avoids low temperature lithium chemistry and which makes use of more readily available and less expensive chiral reagents.

SUMMARY OF THE INVENTION

The present invention provides an improved process for preparing (+)-α-dihydrotetrabenazine in which chirality is introduced at the carbon atom which will become the 2-position of the (+)-α-dihydrotetrabenazine at an earlier stage in the synthesis and the final step in the synthesis is the reduction of a lactam analogue of the dihydrotetrabenazines. The process of the present invention is advantageous with respect to the process disclosed in KR101102957 B1 in that the use of very low temperature lithium chemistry is avoided thereby making the process more suited for operation on a larger scale. The process of the present invention also makes use of a more widely available and less expensive chiral auxiliary in order to form the key chiral 1-allyl-6,7-dimethoxy-tetrahydroisoquinoline intermediate (C).

DETAILED DESCRIPTION OF THE INVENTION

The synthetic route used to make the key chiral 1-allyl-6,7-dimethoxy-tetrahydroisoquinoline intermediate (C), starting from commercially available 2-(3,4-dimethoxyphenyl)ethanol, is shown in Scheme 2 below.

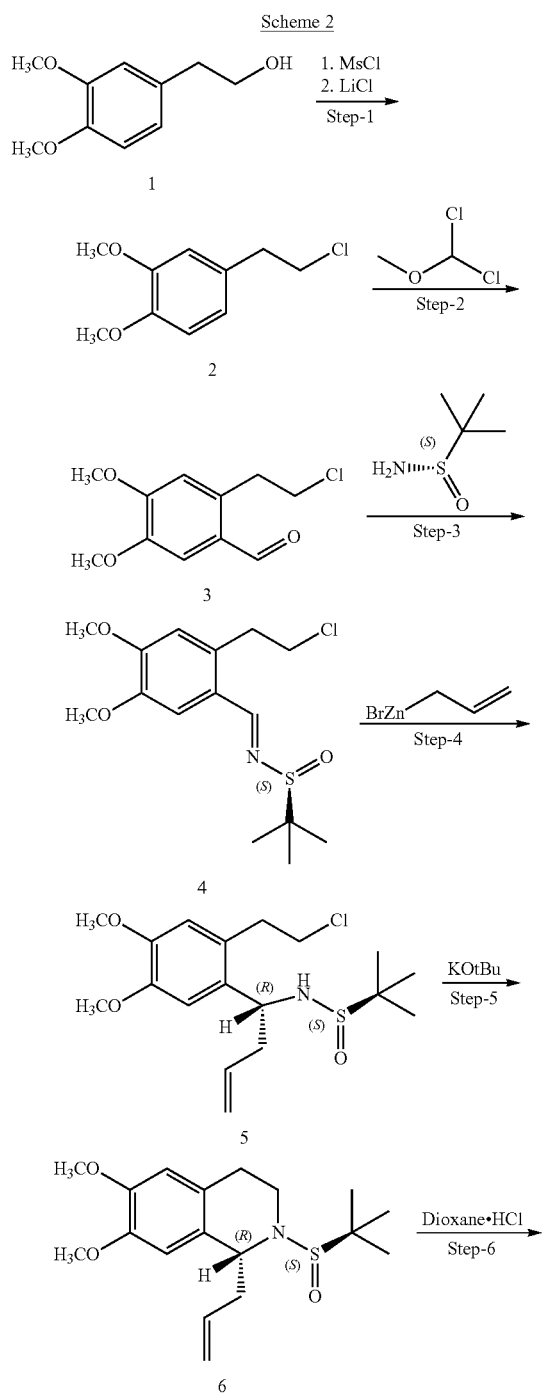

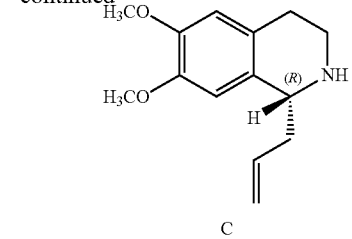

In Schemes 1 and 2 and elsewhere below, the stereochemical configurations of certain of the compounds are indicated in the drawings both by reference to R/S nomenclature and also by the use of wedged and dashed bonds.

A first key step in the synthesis is the reaction of the aldehyde (3) with a chiral sulfinamide, namely (S)-(−)-2-methyl-2-propanesulfinamide, to give the chiral sulfinyl imine (4). Reaction of the sulfinyl imine (4) with an allylic organometallic reagent such as allyl zinc bromide introduces a chiral centre at the benzylic position adjacent the amino group which will ultimately become the 11 b position of the dihydrotetrabenazine. Using allyl zinc bromide ensures that the result of the reaction is a single isomer (5) having an "R" configuration at the benzylic position. By contrast, if a Grignard reagent (allyl magnesium bromide) is used, a mixture of diastereoisomers (having R and S configurations at the benzylic position) is formed, in which case separation of the diastereoisomers would be carried out at this stage rather than carry an unwanted diastereoisomer through subsequent synthetic steps.

The single isomer (5) is subjected to cyclisation in the presence of a non-nucleophilic strong base to give the chiral tetrahydroisoquinoline (6) having an "R" configuration at its 1-position.

By "strong base" is meant a base, the conjugate acid of which has a $pK_a$ of greater than 13.

By "non-nucleophilic" is meant that the base has only modest or negligible activity as a nucleophile in chemical reactions. Such non-nucleophilic bases may be, for example, selected from hydride bases, sterically hindered bases and silicon-based amides.

Examples of non-nucleophilic strong bases that could be used to bring about cyclisation include hindered alkoxide bases such as tert-butoxide bases (e.g. potassium tert-butoxide and sodium tert-butoxide), hydride bases such as sodium hydride and potassium hydride, hindered lithium amide bases such as lithium diisopropylamide (LDA) and lithium tetramethylpiperidide, and silicon-based amide bases such as sodium and potassium bis(trimethylsilyl)amide (NaHMDS and KHMDS respectively).

Preferably the non-nucleophilic strong base is one which can be used at a temperature in excess of −20° C., more usually in excess of 0° C., for example at or around room temperature (e.g. 20° C. to 25° C.).

Currently preferred non-nucleophilic strong bases are hindered alkoxide bases such as tert-butoxide bases (e.g. potassium tert-butoxide and sodium tert-butoxide), with potassium tert-butoxide being a particular example of such a base.

The cyclisation reaction is typically carried out in a polar aprotic solvent such as tetrahydrofuran (THF) or dioxan, with THF being currently preferred.

Following the cyclisation reaction, the chiral sulfinyl group can be removed by mild acid treatment to give the desired chiral 1-allyl-6,7-dimethoxy-tetrahydroisoquinoline intermediate (C). The mild acid treatment may, for example, comprise reaction with an acid selected from hydrochloric acid (HCl), trifluoroacetic acid, (TFA), hydrobromic acid (HBr), hydrofluoric acid (HF), pyridine complex and camphor-10-sulfonic acid (CSA), with HCl currently being preferred. The reaction is typically carried out in solution in a polar solvent such as an ether (e.g. diethyl ether or a cyclic ether such as dioxane) or an alcohol such as methanol, ethanol or isopropyl alcohol.

Accordingly, in a first embodiment (Embodiment 1.1), the invention provides a process for the preparation of a compound of the formula (C):

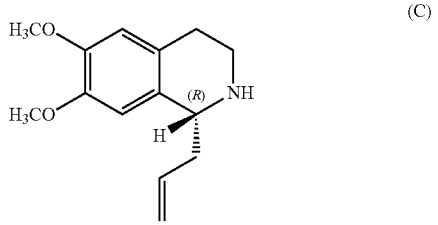

(C)

which process comprises the removal of a tert-butylsulfinyl group from a compound of the formula (6) by reaction with an acid:

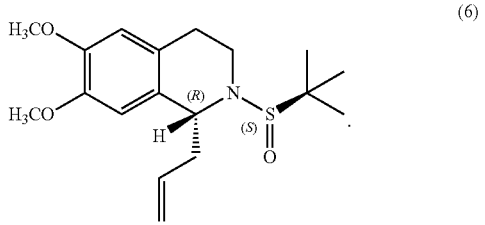

(6)

In further embodiments (Embodiments 1.2 to 1.5), the invention provides:

1.2 A process for the preparation of 1-(R)-allyl-6,7-dimethoxy-1,2,3,4-tetrahydroisoquinoline, which process comprises the removal of a tert-butyl-sulfinyl group from 1-(R)-allyl-2-(tert-butyl-sulfinyl)-6,7-dimethoxy-1,2,3,4-tetrahydroisoquinoline by reaction with an acid.

1.3 A process according to Embodiment 1.2 wherein the tert-butyl-sulfinyl of the 1-(R)-allyl-2-(tert-butyl-sulfinyl)-6,7-dimethoxy-1,2,3,4-tetrahydroisoquinoline has the (S) stereochemical configuration.

1.4 A process according to any one of Embodiments 1.1 to 1.3 wherein the acid is hydrochloric acid.

1.5 A process according to any one of Embodiments 1.1 to 1.4 wherein the reaction is carried out in dioxane.

In another embodiment (Embodiment 2.1), the invention provides a process for the preparation of a compound of the formula (6), which process comprises the cyclisation of a compound of the formula (5):

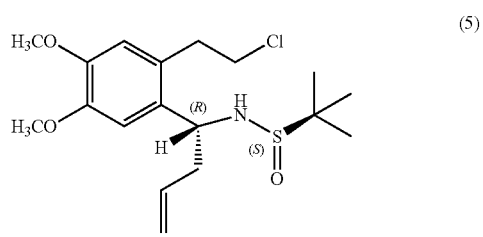

(5)

in the presence of a non-nucleophilic strong base as defined herein.

In further embodiments (Embodiments 2.2 to 2.17), the invention provides:

2.2 A process for the preparation of 1-(R)-allyl-2-(tert-butyl-sulfinyl)-6,7-dimethoxy-1,2,3,4-tetrahydroisoquinoline, which process comprises the cyclisation of N-(1-(2-(2-chloroethyl)-4, 5-dimethoxyphenyl) but-3-en-1-yl)-2-methylpropane-2-sulfinamide in the presence of a non-nucleophilic strong base as defined herein and, where necessary, removing any 1-(S)-allyl-2-(tert-butyl-sulfinyl)-6,7-dimethoxy-1,2,3,4-tetrahydroisoquinoline that may have formed.

2.3 A process according to Embodiment 2.2 wherein the but-3-en-1-yl moiety in the N-(1-(2-(2-chloroethyl)-4, 5-dimethoxyphenyl) but-3-en-1-yl)-2-methylpropane-2-sulfinamide has an (R) stereochemical configuration.

2.4 A process according to Embodiment 2.2 or Embodiment 2.3 wherein the 2-methylpropane-2-sulfinamide moiety in the N-(1-(2-(2-chloroethyl)-4, 5-dimethoxyphenyl) but-3-en-1-yl)-2-methylpropane-2-sulfinamide has an (S) stereochemical configuration.

2.5 A process according to any one of Embodiments 2.1 to 2.4 wherein the non-nucleophilic strong base is a base, the conjugate acid of which has a $pK_a$ of greater than 13.

2.6 A process according to Embodiment 2.5 wherein the non-nucleophilic strong base is selected from hydride bases, sterically hindered nitrogen heterocyclic bases, sterically hindered alkoxides (e.g. tert-butoxide) bases, lithium amide bases and silicon-based amides.

2.7 A process according to Embodiment 2.6 wherein the hydride base is selected from sodium hydride and potassium hydride.

2.8 A process according to Embodiment 2.6 wherein the sterically hindered nitrogen heterocyclic bases are selected from 1,8-diazabicyclo[5.4.0]undec-7-ene (DBU) and 1,5-diazabicyclo[4.3.0]non-5-ene (DBN).

2.9 A process according to Embodiment 2.6 wherein the sterically hindered alkoxides are selected from potassium tert-butoxide and sodium tert-butoxide.

2.10 A process according to Embodiment 2.6 wherein the lithium amide bases and silicon-based amides are selected from lithium diisopropylamide (LDA), lithium tetramethylpiperidide, sodium bis(trimethylsilyl)amide (NaHMDS) and potassium bis(trimethylsilyl)amide (KHMDS).

2.11 A process according to Embodiment 2.6 wherein the non-nucleophilic strong base is selected from potassium tert-butoxide, sodium tert-butoxide, sodium hydride, potassium hydride, lithium diisopropylamide (LDA), lithium tetramethylpiperidide, sodium bis(trimethylsilyl)amide (NaHMDS), potassium bis(trimethylsilyl)amide (KHMDS), 1,8-diazabicyclo[5.4.0]undec-7-ene (DBU) and 1,5-diazabicyclo[4.3.0]non-5-ene (DBN).

2.12 A process according to Embodiment 2.11 wherein the non-nucleophilic strong base is potassium tert-butoxide.

2.13 A process according to any one of Embodiments 2.1 to 2.12 wherein the cyclisation of the compound of the formula (5) is carried out in a polar aprotic solvent.

2.14 A process according to Embodiment 2.13 wherein the polar aprotic solvent is selected from tetrahydrofuran (THF) and dioxane and mixtures thereof.

2.15 A process according to Embodiment 2.14 wherein the polar aprotic solvent is THF.

2.16 A process according to any one of Embodiments 2.1 to 2.15 wherein the cyclisation of the compound of the formula (5) is carried out at a temperature in the range 15° C. to 30° C.

2.17 A process according to any one of Embodiments 2.1 to 2.16 wherein the cyclisation of a compound of the formula (5) is followed by a process step involving the removal of a tert-butyl-sulfinyl group from a compound of the formula (6) as defined in any one of Embodiments 1.1 to 1.5.

In another embodiment (Embodiment 3.1), the invention provides a process for the preparation of a compound of the formula (5), which process comprises the reaction of a compound of the formula (4):

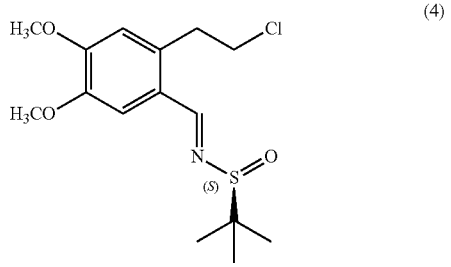

with an allylic organometallic reagent.

In further embodiments (Embodiments 3.2 to 3.12), the invention provides:

3.2 A process for the preparation of N-(1-(2-(2-chloroethyl)-4, 5-dimethoxyphenyl) but-3-en-1-yl)-2-methylpropane-2-sulfinamide, which process comprises the reaction of (E)-N-(2-(2-chloroethyl)-4, 5-dimethoxybenzylidene)-2-methylpropane-2-sulfinamide with an allylic organometallic reagent.

3.3 A process according to Embodiment 3.2 wherein the but-3-en-1-yl moiety in the N-(1-(2-(2-chloroethyl)-4, 5-dimethoxyphenyl) but-3-en-1-yl)-2-methylpropane-2-sulfinamide has an (R) stereochemical configuration.

3.4 A process according to Embodiment 3.2 or Embodiment 3.3 wherein the 2-methylpropane-2-sulfinamide moiety in the (E)-N-(2-(2-chloroethyl)-4, 5-dimethoxybenzylidene)-2-methylpropane-2-sulfinamide has an (S) stereochemical configuration.

3.5 A process according to any one of Embodiments 3.1 to 3.4 wherein the allylic organometallic reagent is selected from allyl magnesium bromide and allyl zinc bromide.

3.6 A process according to Embodiment 3.5 wherein the allylic organometallic reagent is allyl zinc bromide.

3.7 A process according to Embodiment 3.6 wherein the allyl zinc bromide is formed by reacting finely divided (e.g. powdered) zinc with allyl bromide in the presence of an activator for the zinc.

3.8 A process according to Embodiment 3.7 wherein the activator comprises 1,2-dibromoethane.

3.9 A process according to Embodiment 3.8 wherein the activator further comprises trimethylchlorosilane.

3.10 A process according to any one of Embodiments 3.1 to 3.9 wherein the reaction is carried out in a polar non-protic solvent.

3.11 A process according to Embodiment 3.10 wherein the polar aprotic solvent is THF.

3.12 A process according to any one of Embodiments 3.1 to 3.11 wherein the preparation of the compound of the formula (5) is followed by a process step comprising the cyclisation of the compound of the formula (5) as defined in any one of Embodiments 2.1 to 2.14.

In another embodiment (Embodiment 4.1), the invention provides a process for the preparation of a compound of the formula (4) by reaction of a compound of the formula (3):

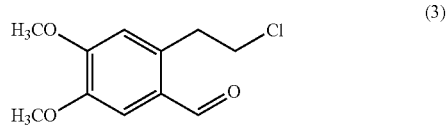 [SMILES: COc1cc(C=O)c(CCCl)cc1OC]

with (S)-(−)-2-methyl-2-propanesulfinamide of the formula:

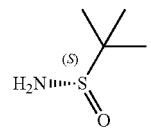

under sulfinyl imine-forming conditions.

In further embodiments (Embodiments 4.2 to 4.8), the invention provides:

4.2 A process for the preparation of (E)-N-(2-(2-chloroethyl)-4, 5-dimethoxybenzylidene)-2-methylpropane-2-sulfinamide, which process comprises the reaction of 2-(2-chloroethyl)-4, 5-dimethoxybenzaldehyde with 2-methyl-2-propanesulfinamide under sulfinyl imine-forming conditions.

4.3 A process according to Embodiment 4.2 wherein the 2-methyl-2-propanesulfinamide is (S)-(−)-2-methyl-2-propanesulfinamide.

4.4 A process according to any one of Embodiments 4.1 to 4.3 wherein the sulfinyl imine-forming conditions comprise the use of a titanium (IV) alkoxide as a dehydrating agent.

4.5 A process according to Embodiment 4.4 wherein the titanium (IV) alkoxide is titanium (IV) ethoxide.

4.6 A process according to any one of Embodiments 4.1 to 4.5 wherein the reaction is carried out in a polar non-protic solvent.

4.7 A process according to Embodiment 4.6 wherein the polar aprotic solvent is THF.

4.8 A process according to any one of Embodiments 4.1 to 4.7 wherein the reaction of the compound of formula (3) with (S)-(−)-2-methyl-2-propanesulfinamide is followed by a process step which comprises the reaction of a compound of the formula (4) with an allylic organometallic reagent as defined in any one of Embodiments 3.1 to 3.12.

In another embodiment (Embodiment 5.1), the invention provides a novel synthetic intermediate which is a compound selected from compounds (4), (5), (5a), (5b) and (6).

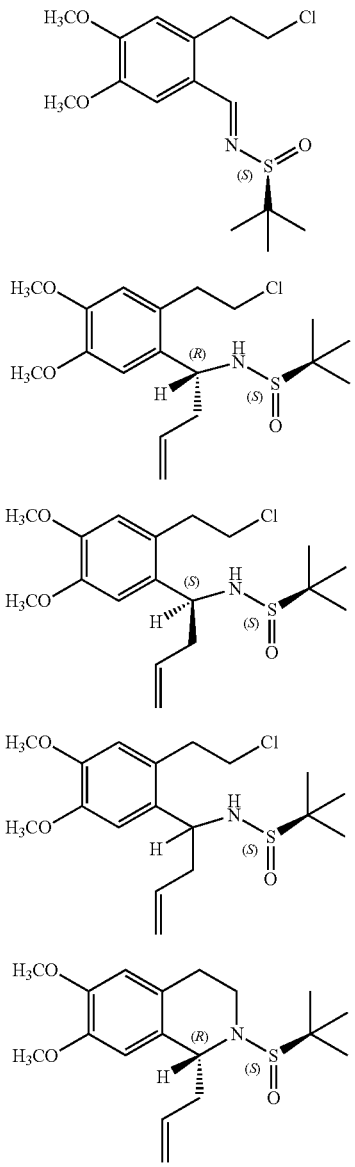

In further embodiments (Embodiments 5.2 to 5.4), the invention provides.

5.2 A compound of the formula (4) as defined in Embodiment 5.1.
5.3 A compound of the formula (5) as defined in Embodiment 5.1.
5.4 A compound of the formula (6) as defined in Embodiment 5.1.
5.5 A compound of the formula (5a) as defined in Embodiment 5.1.
5.6 A compound of the formula (5b) as defined in Embodiment 5.1.

Once formed, the key synthetic intermediate (C) can be transformed in a series of further process steps via intermediates (D), (E), (F), (G) and (H) as shown in Scheme 1 above into (+)-α-dihydrotetrabenazine.

Thus, the N-unsubstituted 1-allyl-tetrahydroisoquinoline (C), can be reacted with 4-methylvaleryl chloride in the presence of a non-interfering base (such as diisopropylethylamine (DIPEA)) to give the amide compound (D).

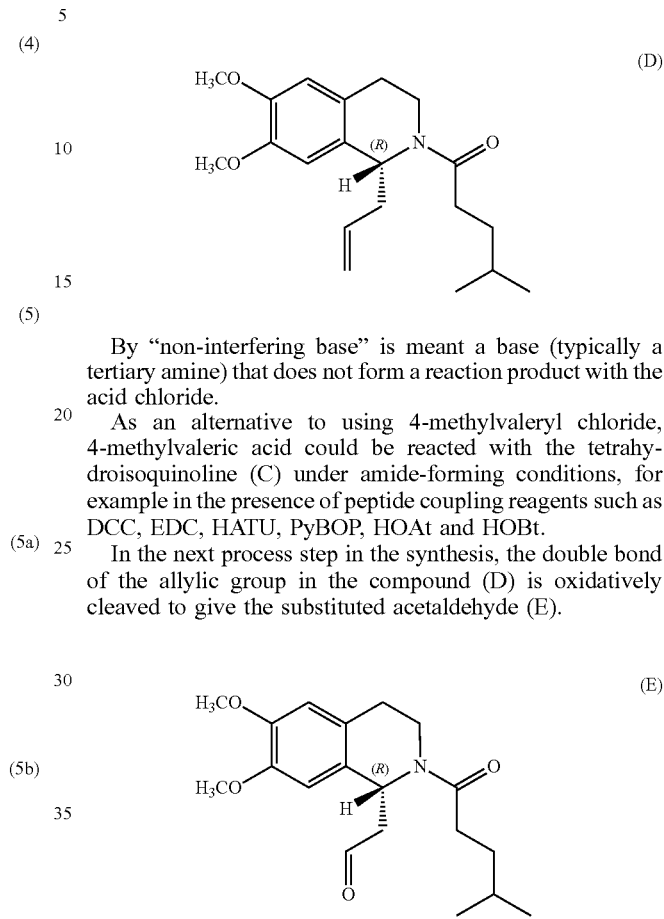

By "non-interfering base" is meant a base (typically a tertiary amine) that does not form a reaction product with the acid chloride.

As an alternative to using 4-methylvaleryl chloride, 4-methylvaleric acid could be reacted with the tetrahydroisoquinoline (C) under amide-forming conditions, for example in the presence of peptide coupling reagents such as DCC, EDC, HATU, PyBOP, HOAt and HOBt.

In the next process step in the synthesis, the double bond of the allylic group in the compound (D) is oxidatively cleaved to give the substituted acetaldehyde (E).

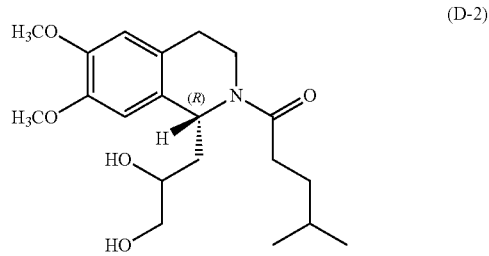

This conversion can proceed in two stages. In a first stage, the amide compound (D) is reacted with an oxidizing agent (e.g. osmium tetroxide) that converts the double bond to a 1,2-diol, to give the intermediate (D-2):

(D-2)

The intermediate (D-2) is then subjected to oxidative cleavage to give the substituted acetaldehyde (E), for example using a periodate such as sodium periodate as the oxidizing agent.

It has been found that the use of osmium tetroxide followed by periodate oxidation gives improved yields and a purer product if 4-methylmorpholine N-oxide (NMO) is included in the reaction mixture with the osmium tetroxide.

The use of Ruthenium catalysts (such as RuCl$_3$) in combination with periodate, or ozonolysis followed by periodate treatment, also give rise to the desired product (E) but the yields are typically lower and multiple impurities are formed.

In the next process step, the substituted acetaldehyde (E) is converted to a silyl enol ether (F) by reaction with tert-butyldimethylsilyl chloride in the presence of a non-interfering base such as DBU. In Intermediate (F), the group "OTBS" is a tert-butyldimethylsilyloxy group.

In the next process step, the silyl enol ether (F) undergoes a [3,3]-sigmatropic rearrangement when treated with isopropyl magnesium chloride to give the 10-membered ring product (G).

The rearrangement of the silyl enol ether (F) is stereospecific and results in the creation of two new chiral centres in which the OTBS and isobutyl groups in the compound (G) are in the configurations required for the end product (+)-α-dihydrotetrabenazine.

In the next process step, treatment of the rearrangement product (G) with an acid such as p-toluenesulfonic acid removes the TBS protecting group to give an intermediate alcohol which further rearranges by ring closure between the nitrogen atom and a carbon atom of the double bond to give the cyclic amide intermediate (H)). This further rearrangement reaction is also highly diastereoselective and results in regeneration of a tetrahydroisoquinoline moiety having R stereochemistry at its 1-position (corresponding to the 11b position in the end product (+)-α-dihydrotetrabenazine).

In the final step in the synthesis, the cyclic amide (H) is reduced to (+)-α-dihydrotetrabenazine using a suitable reducing agent.

A preferred reducing agent is a dialkoxyaluminium hydride and in particular an alkali metal dialkoxyaluminium hydride such as sodium bis (2-methoxyethoxy) aluminum hydride.

Other metal hydrides such as lithium aluminium hydride and sodium borohydride/trifluoroacetic acid also converted the amide (11) to the (+)-α-dihydrotetrabenazine but yields were lower and more impurities were observed.

The stereochemistry of the final dihydrotetrabenazine product is influenced by the stereochemistry of the 2-methyl-2-propanesulfinamide used in Step 3 (Scheme 2) and the use of allyl zinc bromide in Step 4. If (S)-(−)-2-methyl-2-propanesulfinamide is used in Step 3, the stereochemical configuration of the resulting sulfinyl-imine (4) influences the stereochemistries of the subsequent reactions so that, ultimately, the (+)-α-dihydrotetrabenazine isomer is formed in a chiral purity, after recrystallisation, of approximately 100%.

Thus, the present invention provides an improved synthetic process as shown in Schemes 1 and 2 in which the stereochemistry of the final product ((+)-α-dihydrotetrabenazine) is determined by the use of particular chiral reagents at a very early stage in the synthesis. The process avoids the need for wasteful chiral separations in the final step or penultimate step, a problem with known processes for the preparation of (+)-α-dihydrotetrabenazine which have involved either the resolution of racemic mixtures of (±)-α-dihydrotetrabenazine or the resolution of racemic (±)-tetrabenazine followed by a stereospecific reduction.

Accordingly, in a further embodiment (Embodiment 6.1), the invention provides a process for the preparation of (+)-α-dihydrotetrabenazine, which process comprises the preparation of a compound of the formula (C) via a process as defined in any one of Embodiments 1.1 to 4.6, followed by conversion of the compound of formula (C) into a compound of formula (D) as defined herein.

In further embodiments (Embodiments 6.2 to 6.8), the invention provides:

6.2 A process according to Embodiment 6.1 further comprising the conversion of the compound of formula (D) into a compound of the formula (E) as defined herein.
6.3 A process according to Embodiment 6.2 further comprising the conversion of the compound of formula (E) into a compound of the formula (F) as defined herein.
6.4 A process according to Embodiment 6.3 further comprising the conversion of the compound of formula (F) into a compound of the formula (G) as defined herein.
6.5 A process according to Embodiment 6.4 further comprising the conversion of the compound of formula (G) into a compound of the formula (H) as defined herein.
6.6 A process according to Embodiment 6.5 further comprising the conversion of the compound of formula (G) into a compound of the formula (H) as defined herein.
6.7 A process according to Embodiment 6.6 further comprising the conversion of the compound of formula (H) into (+)-α-dihydrotetrabenazine as defined herein.
6.8 A process according to Embodiment 6.7 further comprising bringing the (+)-α-dihydrotetrabenazine into association with (e.g. mixing with) one or more pharmaceutically acceptable excipients to form a pharmaceutical composition.

Isotopes

The compounds described herein may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{11}C$, $^{12}C$, $^{13}C$ and $^{14}C$ and $^{16}O$ and $^{18}O$.

Typically, the compounds described herein do not contain isotopes (such as $^{11}C$ or $^{3}H$) in amounts higher than their natural abundance.

In one embodiment, the percentage of the total hydrogen atoms in the compounds that are deuterium atoms is less than 2%, more typically less than 1%, more usually less than 0.1%, preferably less than 0.05% and most preferably no more than 0.02%.

In an analogous manner, a reference to a particular functional group also includes within its scope isotopic variations, unless the context indicates otherwise.

The isotopes may be radioactive or non-radioactive. In one embodiment of the invention, the compounds described herein contain no radioactive isotopes. Such compounds are preferred for therapeutic use. In another embodiment, however, the (+)-α-dihydrotetrabenazine product of the process of the invention may contain one or more radioisotopes. Compounds containing such radioisotopes may be useful in a diagnostic context.

Solvates

The (+)-α-dihydrotetrabenazine produced by the process of the invention may form solvates.

Examples of solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particular solvates are hydrates, and particular examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

Alternatively, rather than existing as a hydrate, the (+)-α-dihydrotetrabenazine product of the process of the invention may be anhydrous. Therefore, in another embodiment, the (+)-α-dihydrotetrabenazine is in an anhydrous form.

Pharmaceutical Formulations and Methods of Treatment

The (+)-α-dihydrotetrabenazine product of the process of the invention may be formulated as a pharmaceutical composition.

The pharmaceutical composition can be in any form suitable for oral, parenteral, topical, intranasal, intrabronchial, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing the dihydrotetrabenazine compound n can be formulated in accordance with known techniques, see for example, Remington's Pharmaceutical Sciences, Mack Publishing Company, Easton, PA, USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 2 milligrams to 200 milligrams of active ingredient, more usually from 10 milligrams to 100 milligrams, for example, 12.5 milligrams, 25 milligrams and 50 milligrams.

The active compound will be administered to a patient in need thereof (for example a human or animal patient) in an amount sufficient to achieve the desired therapeutic effect.

EXAMPLES

The following non-limiting examples illustrate the synthetic route of the invention.

In the examples, the following abbreviations are used:

| | |
|---|---|
| DCM | dichloromethane |
| DMSO | dimethylsulfoxide |
| DM water | demineralised water |
| eq. | molar equivalents |
| HPLC | High performance liquid chromatography |
| LCMS | Liquid chromatography-mass spectrometry |
| MTBE | methyl tertiary-butyl ether |
| NMR | Nuclear magnetic resonance |
| RT | Room temperature |
| THF | tetrahydrofuran |
| TLC | thin layer chromatography |
| TMS | tetramethylsilane |
| TMS-Cl | trimethylsilyl chloride |
| Vol | volume equivalents |

¹H NMR studies were carried out using a Bruker 400 MHz apparatus. The sample was dissolved in CDCl₃ or DMSO-d₆ with 0.05% tetramethylsilane (TMS) as an internal reference.

The LCMS systems used were as follows:

| LCMS Method | | Method C3 |
|---|---|---|
| Mobile Phase | (A) | 2 mM ammonium acetate followed by 0.1% formic acid in water |
| | (B) | 0.1% formic acid in acetonitrile |
| Instrument | | Agilent 1290 Infinity RRLC attached with Agilent 120 Mass detector and Diode array Detector |
| Column | | BEH C18(50 * 2.1 mm)1.7 μm |
| Flow rate | | 0.550 ml/min |
| Column oven temperature | | Ambient |
| Run time | | 3.0 min |
| Gradient: | | |

| TIME: | Flow Rate (mL/min) | % A | % B |
|---|---|---|---|
| 0.01 | 0.55 | 98 | 2 |
| 0.30 | 0.55 | 98 | 2 |
| 0.60 | 0.55 | 50 | 50 |
| 1.10 | 0.55 | 25 | 75 |
| 2.00 | 0.60 | 0 | 100 |
| 2.70 | 0.60 | 0 | 100 |
| 2.71 | 0.55 | 98 | 2 |
| 3.00 | 0.55 | 98 | 2 |

| LCMS Method | | Euphoria Method |
|---|---|---|
| Mobile Phase | (A) | 0.1% formic acid in water |
| | (B) | 100% methanol |
| Instrument | | Agilent 1290 Infinity RRLC attached with Agilent 6120 Mass detector and Diode array Detector |
| Column | | Phenomenex, Gemini 3 μm C6-Phenyl, 100 * 4.6 mm |
| Flow rate | | 1.00 ml/min |
| Column oven temperature | | Ambient |
| Run time | | 8.0 min |
| Gradient: | | |

| TIME: | Flow Rate (mL/min) | % A | % B |
|---|---|---|---|
| 0.01 | 1.00 | 95 | 5 |
| 3.00 | 1.00 | 20 | 80 |
| 5.00 | 1.00 | 0 | 100 |
| 6.00 | 1.00 | 0 | 100 |
| 6.01 | 1.00 | 95 | 5 |
| 8.00 | 1.00 | 95 | 5 |

| LCMS Method | | Method X |
|---|---|---|
| Mobile Phase | (A) | 2 mM ammonium acetate followed by 0.1% formic acid in water & acetonitrile (90:10) |
| | (B) | 0.1% formic acid in acetonitrile |
| Instrument | | WATERS ACQUETY H Class with PDA and SQ DETECTOR |
| Column | | BEH C18(50 * 2.1 mm) 1.7 μm |
| Flow rate | | 0.600 ml/min |
| Column oven temperature | | Ambient |
| Run time | | 1.5 min |
| Gradient: | | |

| TIME: | Flow Rate (mL/min) | % A | % B |
|---|---|---|---|
| 0.01 | 1.00 | 95 | 5 |
| | 1.00 | 0 | 100 |
| | 1.00 | 0 | 100 |
| | 1.00 | 0 | 100 |
| | 1.00 | 95 | 5 |
| | 1.00 | 95 | 5 |

Step 1

Preparation of 2-(3,4-dimethoxyphenyl)-ethyl chloride (2)

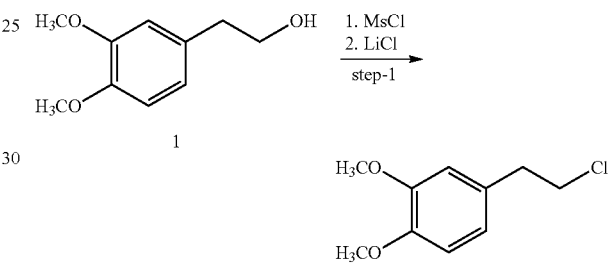

Triethylamine (58.3 g, 0.576 moles, 1.5eq) was added to a stirred solution of (1) 3,4 dimethoxy phenyl ethanol (70 g, 0.3841 moles, 1.0 eq.) in dichloromethane (700 ml, 10 Vols). The reaction mixture was cooled to 0-5° C. and methanesulfonyl chloride (52.89 g, 0.461, 1.2 eq) was added in a dropwise manner. The progress of the reaction was monitored by TLC.

After completion of the reaction, DM water (10 Vol) was added at 0-5° C. and the organic and aqueous layers were separated. The organic layer was washed with DM water (10 Vol), and the organic layer was dried and concentrated under reduced pressure to give 105 g of an intermediate mesylate compound.

The mesylate intermediate (105 g, 1.0 eq.) was in dissolved in THF (700 ml, 10 Vol) and stirred and lithium chloride (32.56 g, 0.768 moles, 2.0 eq.) was added to the stirred solution. The reaction mixture was heated to a temperature of 50-60° C. and maintained at this temperature for 24 hours. The progress of the reaction was monitored by TLC.

After completion of the reaction, the reaction mixture was cooled to 25-30° C. and DM water (10 Vol) and ethyl acetate (10 Vol) were added. The resulting mixture was stirred for 20 minutes and the organic and aqueous layers were then separated. The organic layer was washed with DM water (10 Vol), and the organic layer was dried and concentrated under reduced pressure to give 77 g (100% yield) of 2-(3,4-dimethoxy-phenyl)-ethyl chloride (2).

¹H NMR (400 MHz, Chloroform-d) −δ 6.84 (d, J=8.0 Hz, 1H), 6.79-6.76 (m, 2H), 3.89 (d, J=6.3 Hz, 6H), 3.71 (t, J=7.4 Hz, 2H), 3.03 (t, J=7.5 Hz, 2H).

m/z: [M+H]⁺ found: 201.13.

Step 2

Preparation of 2-(2-chloroethyl)-4,5-dimethoxybenzaldehyde (3)

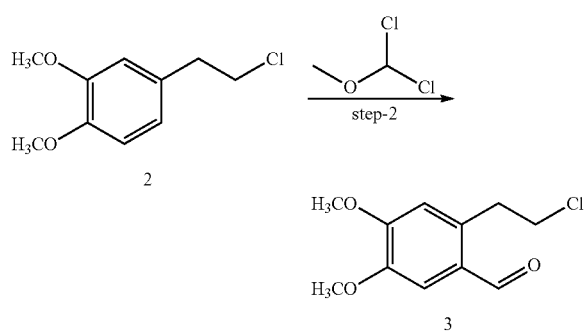

A stirred solution of (2) (77 g, 0.385 moles, 1.0 eq.) in dichloromethane (770 ml, 10 Vols) at room temperature was cooled to −20 to −15° C. and dichloromethyl methyl ether (48.6 g, 0.422 moles, 1.1 eq.) was added. Titanium chloride (182.5 g, 0.962 moles, 2.5 eq.) was added in a dropwise manner, maintaining the temperature at −20 to −15° C. The reaction mixture was allowed to come to room temperature and was stirred for 24 hours, the progress of the reaction during this time being monitored by TLC.

After completion of the reaction, 0.2 N aqueous HCl solution (20 Vol) was added at −20 to −15° C. The temperature of the reaction mixture was raised to RT and the organic and aqueous layers were separated. The aqueous layer was extracted with 10 Vol dichloromethane. Both organic layers were combined and washed with 2×10 Vol saturated sodium bicarbonate solution at room temperature, followed by DM water (10 Vol). The organic layer was then dried and concentrated under reduced pressure to give 118.0 g of crude intermediate (3).

The crude product (118.0 g) was dissolved in 231.0 ml (3 Vol) ethyl acetate and reprecipitated in n-hexane 1.15 L (15 Vol). The resulting solid was filtered and dried under reduced pressure at 45-50° C. Weight of pure (3): 77.0 g (87.69% yield)

$^1$H NMR (400 MHz, Chloroform-d) −δ 10.15 (s, 1H), 7.39 (s, 1H), 6.82 (s, 1H), 4.04-3.91 (m, 6H), 3.79 (t, J=7.0 Hz, 2H), 3.47 (t, J=7.0 Hz, 2H).

LCMS: m/z: [M+H]$^+$; found: 229.2 Retention Time: 1.59 Method C3

Step 3

Preparation of (E)-N-(2-(2-chloroethyl)-4,5-dimethoxybenzylidene)-2-methylpropane-2-sulfinamide (4)

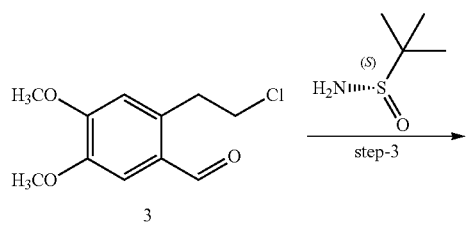

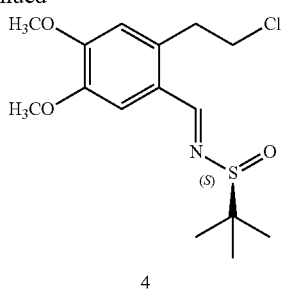

To a stirred solution of (3) (25 g, 0.109 moles, 1.0 eq) in THF (250 ml, 10 Vol) at room temperature was added titanium ethoxide (27.4 g, 0.120 moles, 1.1 eq). With the temperature being maintained at room temperature, (S)-(−)-2-methyl-2-propanesulfinamide (24.4 g, 0.201 moles, 1.8 eq) was added to the mixture which was then heated to 60 to 65° C. The reaction mixture was stirred for 2-3 hrs at 60 to 65° C. and the progress of the reaction was monitored by TLC. After completion of the reaction, the reaction mixture was cooled to room temperature and saturated sodium bicarbonate solution (10 Vol) and ethyl acetate (10 Vol) were added.

The reaction mixture was filtered through a Celite bed which was then washed with ethyl acetate (3 Vol) and the organic layer and aqueous layer were then separated. The organic layer was washed with DM water (10 Vol), dried and concentrated under reduced pressure to get 40.0 g of crude Intermediate (4).

The crude product (40.0 g) was dissolved in MTBE (1 Vol) and re-precipitated in n-hexane (10 Vols). The resulting solid was collected by filtration and dried under reduced pressure at 45-50° C. to give 36.0 g (100% yield) of purified Intermediate (4).

$^1$H NMR (400 MHz, Chloroform-d) −δ 8.70 (s, 1H), 7.43 (s, 1H), 6.80 (s, 1H), 3.97-3.89 (m, 6H), 3.77-3.67 (m, 2H), 3.47-3.36 (m, 2H), 1.27 (s, 9H).

LCMS: m/z: [M+H]$^+$; found: 332.25 Retention Time: 1.73—Method C3

Step 4

Preparation of N-(1-(2-(2-chloroethyl)-4,5-dimethoxyphenyl) but-3-en-1-yl)-2-methylpropane-2-sulfinamide (5)

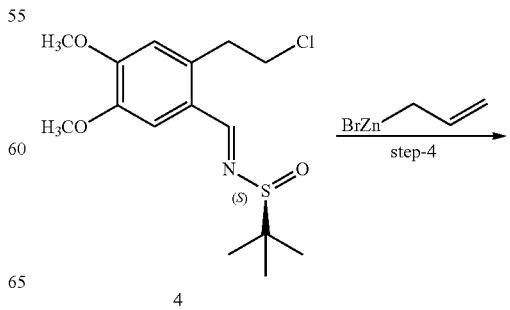

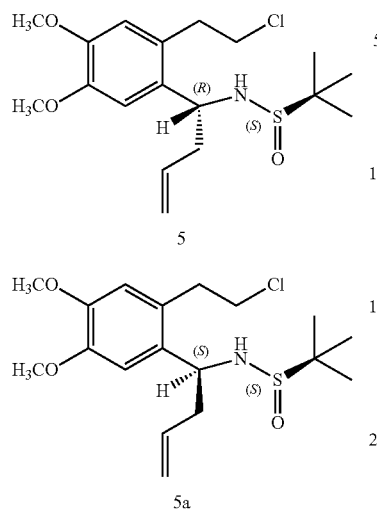

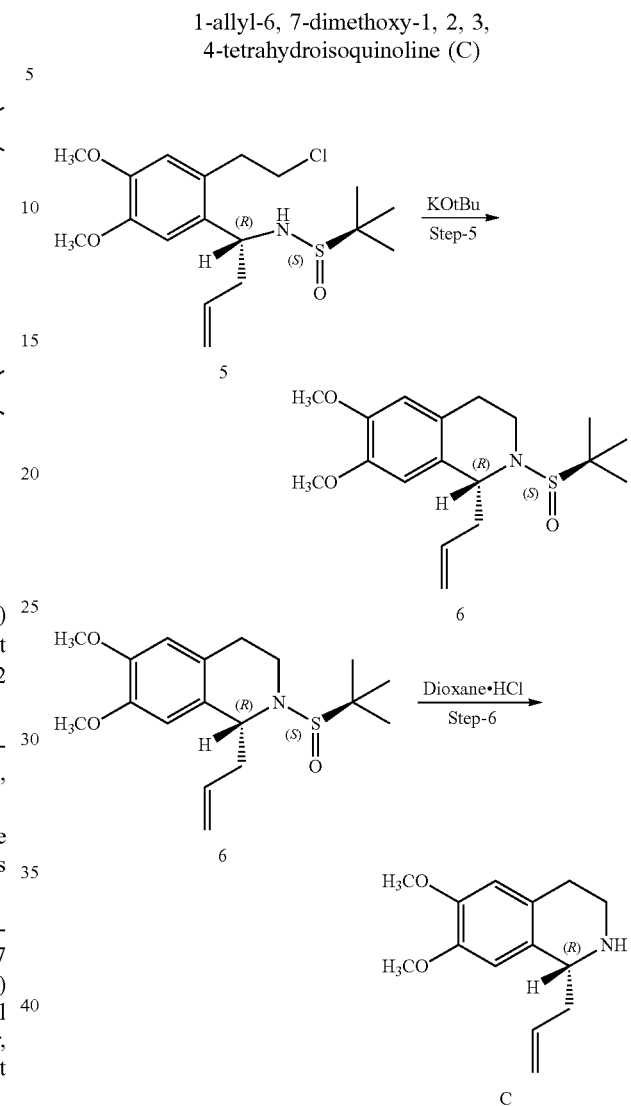

Steps 5 and 6

1-allyl-6, 7-dimethoxy-1, 2, 3, 4-tetrahydroisoquinoline (C)

A stirred mixture of zinc dust (74 g, 1.13 moles, 10.0 eq) in THF (370 ml, 10 Vol) under a protective nitrogen blanket at room temperature was heated to 55-60° C. and 1,2 dibromoethane (7.3 ml, 0.018 moles, 0.16 eq) was added.

TMS-Cl (1.7 ml, 0.018 moles, 0.16 eq) was added dropwise at 55-60° C., following which allyl bromide (80 ml, 0.05 moles, 4.5 eq) was also dropwise at 55-60° C.

After the addition of the reactants was complete, the reaction mixture was maintained at 55-60° C. for 1-2 hours before cooling to room temperature.

In a separate flask, (E)-N-(2-(2-chloroethyl)-4, 5-dimethoxybenzylidene)-2-methylpropane-2-sulfinamide (4) (37 g, 0.111, 1.0 eq) was dissolved in THF (370 ml, 10 Vol) under nitrogen at room temperature. The solution of allyl zinc bromide in THF was then added in a dropwise manner, following which the reaction mixture was maintained at room temperature for 2-3 hours and monitored by TLC.

After completion of the reaction, the reaction mixture was cooled to −5 to 0° C. and DM water (10 Vol) was dropwise at −5 to 0° C., following which Celite® (60 g Celite) was added and the mixture was filtered through a bed of Celite. To the filtrate was added ethyl acetate (10 Vol) and the mixture was stirred for 10-15 minutes.

The organic and aqueous layers were separated, and the aqueous layer was extracted with ethyl acetate (5 Vol). The organic layer was washed with DM water (10 Vol), dried and then concentrated under reduced pressure to give the title compound (5) (41.0 g) Yield: 98.3%

$^1$H NMR (400 MHz, Chloroform-d) −δ 6.91 (s, 1H), 6.71 (s, 1H), 5.85-5.73 (m, 1H), 5.29-5.18 (m, 2H), 5.12-5.01 (m, 1H), 4.66 (dd, J=8.6, 5.7 Hz, 1H), 3.91-3.77 (m, 6H), 3.77 (s, 2H), 3.23-3.06 (m, 2H), 2.65-2.41 (m, 2H), 1.23 (s, 9H).

LCMS: m/z: [M+H]$^+$; found: 374.6 Retention Time: 1.63 Method C3

Note: in early feasibility experiments, allyl magnesium bromide was used instead of allyl zinc bromide but gave a mixture of diastereoisomers (5) and (5a) whereas allyl zinc bromide gave predominantly the isomer of interest (5).

To a stirred solution (5) (41 g, 0.1099 mol, 1.0 eq) in THF (410 ml, 10 Vol) under a nitrogen blanket at room temperature was added potassium tert-butoxide (24.66 g, 0.219 mol, 2.0 eq) at room temperature and the reaction mixture was maintained at room temperature for 1-2 hours. DM water (10 Vol) was then added in a dropwise manner at 10-15° C., followed by ethyl acetate (10 Vol) and the mixture was stirred for 10-15 minutes before separating the organic and aqueous layers and extracting the aqueous layer with ethyl acetate (5 Vol). The combined organic layers were washed with DM water (10 Vol), dried and concentrated under reduced pressure to give 41.0 g of intermediate compound (6) as an oily residue which was used without further purification Intermediate (6) was dissolved in ethyl acetate (10 Vol) and dioxane HCl (4M) (1.5 Vol) was dropwise at 15 to 20° C. The reaction mixture was maintained at room temperature for an hour and the resulting solid hydrochloride salt of Compound (C) was isolated by filtration and washed with ethyl acetate (2 Vol).

The hydrochloride salt of Compound (C) was dissolved in DM water (10 Vol), ethyl acetate (5 Vol) was added and the mixture was stirred for 10-15 minutes. The organic and aqueous layers were separated and the aqueous layer was extracted with ethyl acetate (5 Vol). The pH of the aqueous layer was adjusted to pH 10-11 using sodium carbonate solution and the aqueous layer was then extracted with 2×10 Vol dichloromethane. The combined organic layers were washed with DM water (10 Vol), dried and concentrated under reduced pressure to give 18.0 g of compound (C).

$^1$H NMR (400 MHz, Chloroform-d) −δ 6.68 (s, 1H), 6.60 (s, 1H), 5.91-5.81 (m, 1H), 5.23-5.15 (m, 2H), 4.01 (s, 1H), 3.88 (s, 6H), 3.27-3.21 (s, 1H), 3.00-2.96 (m, 1H), 2.81-2.64 (m, 3H), 2.55-2.45 (m, 1H).

LCMS: m/z: [M+H]$^+$; found: 234.5 Retention Time: 1.30 Method C3

Step 7

1-(1-allyl-6, 7-dimethoxy-3, 4-dihydroisoquinolin-2 (1H)-yl)-4-Methylpentan-1-one (D)

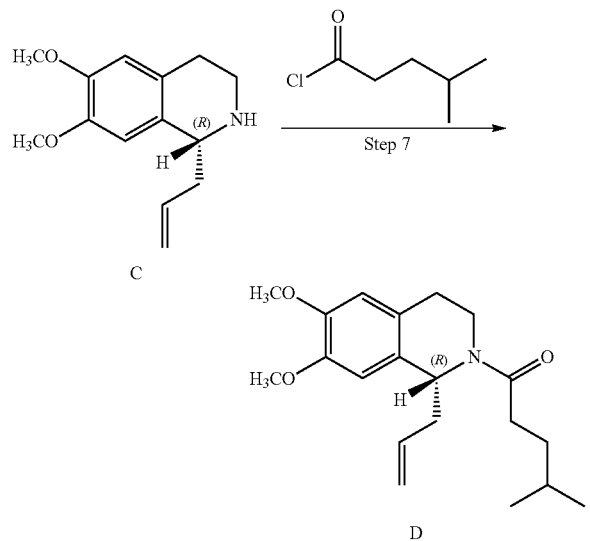

C

D

To a stirred solution of (C) (18 g, 0.077 mol, 1.0 eq) in DCM (10 Vol) under nitrogen blanket at room temperature was added diisopropylethylamine (20 g, 0.154 mol, 2.0 eq). 4-Methylvaleryl chloride (11.34 g, 0.084 mol, 1.1 eq) was added in a dropwise manner at 10-15° C. and the reaction mixture was maintained at room temperature for 1-2 hours. The progress of the reaction was monitored by TLC.

When it was adjudged that the reaction was complete, DM water (10 Vol) was added and the mixture was stirred for 10-15 minutes. The organic and aqueous layers were separated, and the aqueous layer was extracted with DCM (5 Vol). The combined organic layers were washed with DM water (10 Vol), dried and concentrated under reduced pressure to give crude title compound (D), 25.0 g—Yield: 97.77%. In repeat experiments, the purity of the crude compound (D) ranged from 80.65% to 98.06%.

The crude compound (D) was used in the next step without further purification.

$^1$H NMR (400 MHz, Chloroform-d) −δ 6.68-6.58 (m, 2H), 5.86 (dd, J=17.7, 8.9 Hz, 1H), 5.70-5.61 (m, 1H), 5.03 (d, J=13.4 Hz, 1H), 4.92-4.63 (m, 1H), 3.89 (m, 6H), 3.56-3.51 (m, 1H), 3.04 (d, J=10.9 Hz, 1H), 2.87 (dd, J=11.0, 5.6 Hz, 1H), 2.76 (d, J=15.8 Hz, 1H), 2.58-2.54 (m, 2H), 2.49-2.31 (m, 1H), 1.56 (q, J=7.7 Hz, 4H), 0.93 (dd, J=10.1, 6.2 Hz, 6H).

LCMS: m/z: [M+H]+; found: 332.2 Retention Time: 1.81 Method C3

Step 8

2-(6, 7-dimethoxy-2-(4-methylpentanoyl)-1, 2, 3, 4-tetrahydroisoquinolin-1-yl) acetaldehyde (E)

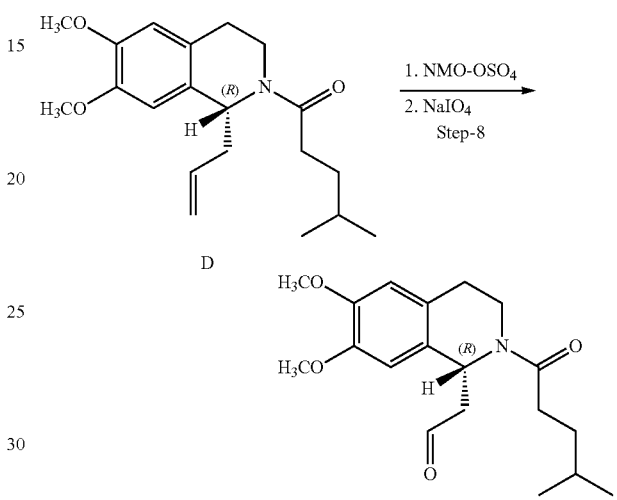

D

E

To a stirred solution of Intermediate (D) (27 g, 0.0814 moles, 1.0 eq) in acetone (270 ml, 10 Vol) and DM water (67.5 ml, 10Vol) under nitrogen blanket at RT was added osmium tetroxide (0.82 g, 0.0032, 0.04 eq) at RT.

4-Methylmorpholine N-oxide (57.5 ml of a 50% solution, 0.244 moles, 3.0 eq) was then added and the reaction mixture was maintained for the next 24 hours at RT, and the reaction monitored by TLC for formation of the intermediate diol product. After completion, the reaction was quenched with (10 Vol water), extracted with dichloromethane twice and the combined organic layers were washed twice with water.

Sodium periodate (52.14 g, 0.244 moles, 3.0 eq) was added to the organic layer and the reaction mixture was maintained at RT and monitored by TLC for formation of the aldehyde product.

When the reaction was judged to be complete, DM water (10 Vol) and DCM (20 Vol) were added and the mixture was stirred for 10-15 minutes. The organic and aqueous layers were then separated and the aqueous layer was extracted with DCM (5 Vol). The combined organic layers were washed with DM water (10 Vol), dried and concentrated under reduced pressure to afford 30 g of crude Intermediate (E) which was used in the next step without further purification.

$^1$H NMR (400 MHz, Chloroform-d) −δ 9.90-9.80 (m, 1H), 6.68 (s, 1H), 6.61 (s, 1H), 6.06 (dd, J=9.4, 4.6 Hz, 1H), 3.88 (s, 6H), 3.57-3.50 (m, 1H), 2.97-2.83 (m, 2H), 2.81-2.70 (m, 2H), 2.46-2.32 (m, 2H), 1.65-1.45 (m, 4H), 0.93 (dd, J=6.6, 3.3 Hz, 6H).

LCMS: m/z: [M+H]$^+$; found: 334.0 Retention Time: 4.92 Euphoria Method

Step 9

1-(1-(2-((tert-butyldimethylsilyl) oxy) vinyl)-6, 7-dimethoxy-3, 4-dihydroisoquinolin-2(1H)-yl)-4-methylpentan-1-one (F)

Step 10

(5S, 6R, E)-6-((tert-butyldimethylsilyl) oxy)-5-isobutyl-10, 11-dimethoxy-2, 3, 5, 6-tetrahydrobenzo[d]azecin-4(1H)-one (G)

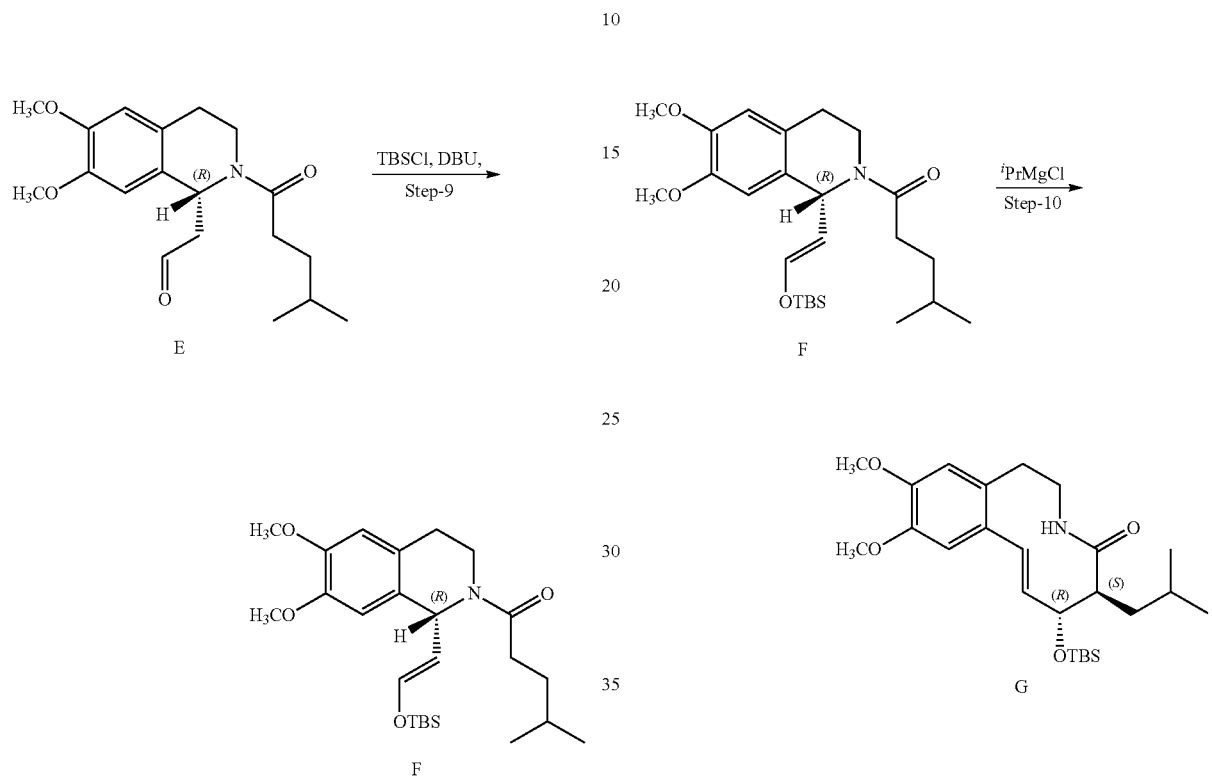

A stirred solution of Intermediate (E) (30 g, 0.09006 moles, 1.0 eq) in DCM (300 ml, 10 V) under a nitrogen blanket was cooled to 10-15° C. and was charged with 1,8-diazabicyclo [5.4.0] undec-7-ene (27.4 g, 0.1799 moles, 2.0 eq). tert-Butyldimethylsilyl chloride (24.3 g, 0.1612 moles, 1.8 eq) was then added and the reaction mixture was maintained for 1-2 hours at 10-15° C., and monitored by TLC.

When it was judged that the reaction was complete, DM water (10 Vol) was added and the mixture was stirred for 10-15 minutes. The organic and aqueous layers were separated and the aqueous layer was extracted with DCM (5 Vol). The combined organic layers were washed with DM water (10 Vol), dried and concentrated under reduced pressure to give 34.0 g of Intermediate (F) (Yield: 84.4%) which was used in Step 10 without further purification.

$^1$H NMR (400 MHz, Chloroform-d) –δ 6.62 (d, J=7.9 Hz, 2H), 6.50-6.40 (m, 1H), 6.04-6.02 (m, 1H), 5.24 (d, J=8.3 Hz, 1H), 3.99-3.88 (m, 1H), 3.92-3.83 (m, 6H), 3.49 (s, 1H), 3.01-2.64 (m, 2H), 2.70 (dd, J=30.1, 15.9 Hz, 2H), 2.47-2.36 (m, 3H), 1.08-0.91 (m, 15H), 0.15 (d, J=10.4 Hz, 6H).

LCMS: m/z: [M+H]$^+$; found: 447.6 Retention Time: 2.32 Method C3

A 2M solution of isopropylmagnesium chloride (38.59 g, 0.375 moles, 3.0 eq) in THF (187.6 mL) was added in a dropwise manner to a stirred solution of Intermediate (F) (56 g, 0.1254 moles, 1.0 eq) in toluene (20 Vol) under nitrogen blanket at RT and the reaction mixture was then heated to 85-90° C. The reaction mixture was maintained at 85-90° C. for the next 5-6 hours, and the reaction was monitored by TLC during this time. When it was judged that reaction was complete, the reaction mixture was cooled to 0-5° C., DM water (10 Vol) was added dropwise and the mixture was stirred for 10-15 minutes before filtering through a Celite® bed and washing the Celite bed with toluene (5 Vol). The organic and aqueous layers were separated and the aqueous layer was extracted with toluene (5 Vol). The combined organic layers were then washed with DM water (10 Vol), dried and concentrated under reduced pressure to give 56 g of Intermediate (G) (Crude yield: 100%)

$^1$H NMR (400 MHz, Chloroform-d) –δ 6.77 (s, 1H), 6.69 (s, 1H), 6.60-6.56 (m, 2H), 5.44 (dd, J=16.5, 8.2 Hz, 1H), 5.13 (dd, J=8.2, 5.1 Hz, 1H), 4.19 (t, J=8.7 Hz, 1H), 4.03-4.02 (m, 1H), 3.94-3.85 (m, 6H), 3.50-3.38 (m, 1H), 2.84-2.67 (m, 1H), 2.30-2.27 (m, 1H), 1.89-1.75 (m, 2H), 1.60-1.38 (m, 2H), 0.98-0.85 (m, 15H), 0.14 (s, 9H).

LCMS: m/z: [M+H]$^+$; found: 448.5 Retention Time: 2.38 Method C3

Step 11

(2R,3S,11bR)-2-hydroxy-3-isobutyl-9,10-dimethoxy-1,2,3,6,7,11b-hexahydro-4H-pyrido[2,1-a]isoquinolin-4-one (H)

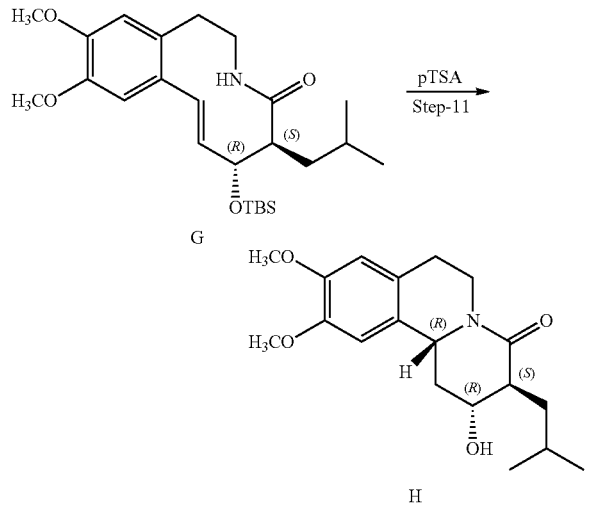

p-Toluenesulfonic acid monohydrate (35.74 g, 0.187 moles, 1.5eq) was added to a stirred solution of Intermediate (G) (56 g, 0.1250 moles, 1.0 eq) in toluene (448.0 ml, 8.0 Vol) acetonitrile (112.0 ml, 2.0 Vol) under a nitrogen blanket at RT and the reaction mixture was maintained at RT for 12-14 hours. After TLC had indicated that the reaction had gone to completion, saturated sodium bicarbonate solution (10 Vol) was added (dropwise) and the mixture was stirred for 10-15 minutes. The resulting mixture was extracted with ethyl acetate (2×10 Vol) and the combined organic layers were washed with DM water (10 Vol), dried and concentrated under reduced pressure to give crude Intermediate (H). The crude product was subjected to column chromatography (silica gel, ethyl acetate:n-hexane 3:7) to give pure Intermediate (H) (18.3 g—Yield: 43.92%)

$^1$H NMR (400 MHz, Chloroform-d) −δ 6.70 (s, 1H), 6.66 (s, 1H), 4.89-4.79 (m, 1H), 4.67 (dd, J=11.5, 4.2 Hz, 1H), 3.97 (td, J=16.1, 14.3, 8.1 Hz, 2H), 3.91 (s, 6H), 2.97-2.84 (m, 1H), 2.87-2.73 (m, 2H), 2.72-2.62 (m, 1H), 2.34 (dt, J=9.9, 5.6 Hz, 1H), 1.98-1.74 (m, 2H), 1.63-1.60 (m, 1H), 1.00 (dd, J=24.3, 6.5 Hz, 6H).

LCMS: m/z: [M+H]$^+$; found: 334.3 Retention Time: 1.53 Method C3

Step 12

(2R,3R,11bR)-3-isobutyl-9,10-dimethoxy-1,3,4,6,7,11b-hexahydro-2H-pyrido[2,1-a]isoquinolin-2-ol ((+)-α-dihydrotetrabenazine)

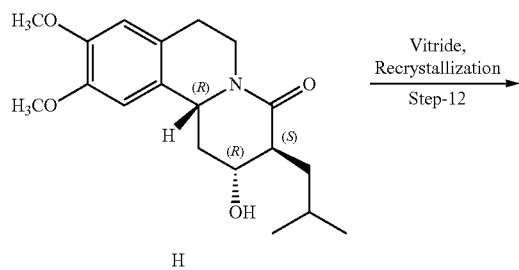

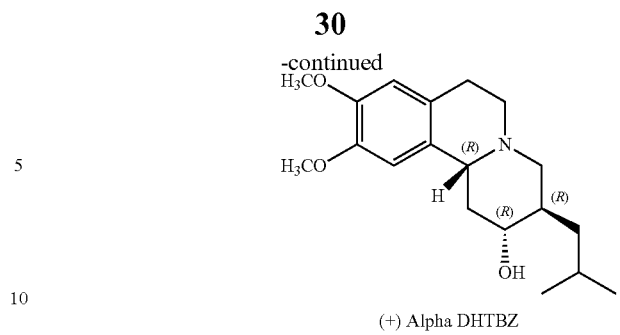

To a stirred solution of Intermediate (H) (18 g, 0.0539 moles, 1.0 eq) in toluene (360 ml, 20 V) under a nitrogen blanket at 0-10° C. was added (dropwise) sodium bis(2-methoxyethoxy)aluminium dihydride (Vitride) (65.3 g, 0.323 moles, 6.0 eq) (70% in toluene). After addition was complete, the reaction mixture was heated to 85-90° C. and maintained at this temperature for 2-4 hours, with monitoring by TLC. The reaction mixture was then cooled to 5-10° C. and ethyl acetate (3 Vol) was added in a dropwise manner, care being taken to keep the temperature below 25° C. 10% Sodium hydroxide solution (10 Vol) was then added dropwise, keeping the temperature below 25° C. and the resulting mixture was extracted with ethyl acetate (3×10 Vol). The combined organic layers were washed with DM water (10 Vol), dried and concentrated under reduced pressure to give 16.3 g of crude title compound.

The crude title compound was subjected to column chromatography using silica gel (100-200 mesh) and 60% ethyl acetate in n-hexane as mobile phase to afford 9.2 g of pure title compound (Yield: 53.36%)

Alternative Method of Purifying ((+)-α-dihydrotetrabenazine)

Acetone (14.4 ml) (3 V) was added to a stirred slurry of (+)-α-dihydrotetrabenazine (4.8 g, 0.01502 moles, 1.0 eq) in DM water (3 Vol) under a nitrogen blanket at RT. The mixture was heated to 50-55° C. and maintained at this temperature for 1 hour, following which it was cooled to 25-30° C. The mixture was filtered to isolate the solids which dried under vacuum at 50-55° C. to give 3.5 of pure (+)-α-dihydrotetrabenazine (Yield: 72.9%)

$^1$H NMR (400 MHz, DMSO-d6) −δ 6.71 (s, 1H), 6.63 (s, 1H), 4.62 (d, J=6 Hz, 1H), 3.89 (s, 6H), 3.19 (s, 1H), 3.14-2.82 (m, 4H), 2.54 (d, J=11.9 Hz, 2H), 1.85-1.72 (m, 1H), 1.72-1.61 (m, 3H), 1.59 (d, J=10.8 Hz, 1H), 1.11 (dd, J=13.5, 9.8 Hz, 1H), 0.98 (dd, J=8.6, 6.4 Hz, 6H).

LCMS: m/z: [M+H]$^+$; found: 320.3. Retention Time: 0.77 Method X

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A process for the preparation of a compound of the formula (5)

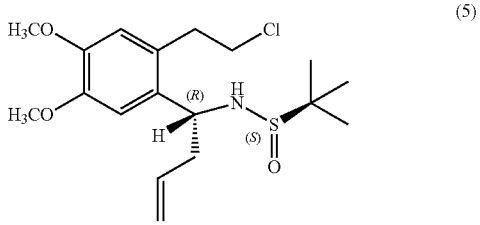

which process comprises the reaction of a compound of the formula (4):

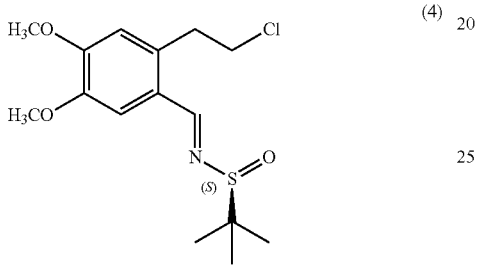

with allyl zinc bromide.

2. A process according to claim 1 wherein the allyl zinc bromide is formed by reacting finely divided (e.g. powdered) zinc with allyl bromide in the presence of an activator for the zinc.

3. A process according to claim 2 wherein the activator comprises 1,2-dibromoethane.

4. A process according to claim 3 wherein the activator further comprises trimethylchlorosilane.

5. A process according to claim 1 wherein the reaction is carried out in a polar non-protic solvent.

6. A process according to claim 5 wherein the polar aprotic solvent is THF.

7. A process according to claim 1 wherein the preparation of the compound of the formula (5) is followed by a process step comprising the cyclisation of the compound of the formula (5) in the presence of a non-nucleophilic strong base to give a compound of the formula (6):

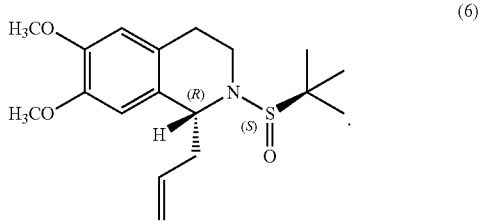

8. A process according to claim 7 wherein the non-nucleophilic strong base is a base, the conjugate acid of which has a pK$_a$ of greater than 13.

9. A process according to claim 8 wherein the non-nucleophilic strong base is selected from hydride bases, sterically hindered nitrogen heterocyclic bases, sterically hindered alkoxides (e.g. tert-butoxide) bases, lithium amide bases and silicon-based amides.

10. A process according to claim 9 wherein the non-nucleophilic strong base is potassium tert-butoxide.

11. A process according to claim 7 wherein the cyclisation of the compound of the formula (5) is carried out in a polar aprotic solvent such as THF.

12. A process according to claim 7 which further comprises the removal of the tert-butyl-sulfinyl group from the compound of the formula (6) by reaction with an acid to give a compound of the formula (C):

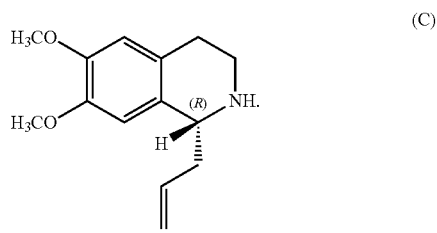

13. A process for the preparation of N-(1-(2-(2-chloroethyl)-4, 5-dimethoxyphenyl) but-3-en-1-yl)-2-methylpropane-2-sulfinamide, wherein the 1-position of the but-3-en-1-yl moiety in the N-(1-(2-(2-chloroethyl)-4, 5-dimethoxyphenyl) but-3-en-1-yl)-2-methylpropane-2-sulfinamide has an (R) stereochemical configuration; and the 2-methylpropane-2-sulfinamide moiety in the (E)-N-(2-(2-chloroethyl)-4, 5-dimethoxybenzylidene)-2-methylpropane-2-sulfinamide has an (S) stereochemical configuration;

which process comprises the reaction of (S)-(E)-N-(2-(2-chloroethyl)-4, 5-dimethoxybenzylidene)-2-methylpropane-2-sulfinamide with allyl zinc bromide.

14. A process according to claim 13 wherein the allyl zinc bromide is formed by reacting finely divided (e.g. powdered) zinc with allyl bromide in the presence of an activator for the zinc such as an activator comprising 1,2-dibromoethane.

15. A process according to claim 14 wherein the activator comprises 1,2-dibromoethane and trimethylchlorosilane.

16. A process according to claim 13 wherein the N-(1-(2-(2-chloroethyl)-4, 5-dimethoxyphenyl) but-3-en-1-yl)-2-methylpropane-2-sulfinamide thus prepared is cyclized in the presence of a non-nucleophilic strong base selected from hindered alkoxide bases to give (1R)-1-allyl-2-((S)-tert-butyl-sulfinyl)-6,7-dimethoxy-1,2,3,4-tetrahydroisoquinoline.

17. A process according to claim 16 wherein the hindered alkoxide bases are selected from tert-butoxide bases such as potassium tert-butoxide and sodium tert-butoxide.

18. A process according to claim 16 which further comprises the removal of the (S)-tert-butyl-sulfinyl group from the 1-(R)-allyl-2-((2S)-tert-butyl-sulfinyl)-6,7-dimethoxy-1, 2,3,4-tetrahydroisoquinoline by reaction with an acid to give 1-(R)-allyl-6,7-dimethoxy-1,2,3,4-tetrahydroisoquinoline.

* * * * *